United States Patent
Sakagawa et al.

(10) Patent No.: US 10,709,329 B2
(45) Date of Patent: Jul. 14, 2020

(54) IMAGE PICKUP APPARATUS AND METHOD OF CONTROLLING IMAGE PICKUP APPARATUS

(71) Applicant: CANON KABUSHIKI KAISHA, Tokyo (JP)

(72) Inventors: Wataru Sakagawa, Kawasaki (JP); Yuki Shimozato, Tokyo (JP); Tomoyuki Ikegami, Hiratsuka (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/218,191

(22) Filed: Jul. 25, 2016

(65) Prior Publication Data

US 2017/0027443 A1    Feb. 2, 2017

(30) Foreign Application Priority Data

Jul. 30, 2015 (JP) .................................. 2015-150573
Jul. 21, 2016 (JP) .................................. 2016-142945

(51) Int. Cl.
*A61B 3/14* (2006.01)
*A61B 3/12* (2006.01)
*A61B 3/00* (2006.01)
*A61B 3/10* (2006.01)

(52) U.S. Cl.
CPC .......... *A61B 3/1225* (2013.01); *A61B 3/0025* (2013.01); *A61B 3/1025* (2013.01); *A61B 3/14* (2013.01)

(58) Field of Classification Search
CPC .......... A61B 3/102; A61B 3/1225; A61B 3/14
USPC ....................................................... 351/206
See application file for complete search history.

(56) References Cited

U.S. PATENT DOCUMENTS

| | | | |
|---|---|---|---|
| 9,326,681 B2 | 5/2016 | Shimozato | |
| 2008/0174734 A1* | 7/2008 | Shimizu | A61B 3/1015 351/206 |
| 2011/0043661 A1* | 2/2011 | Podoleanu | A61B 3/102 348/239 |
| 2013/0003018 A1* | 1/2013 | Utagawa | A61B 3/102 351/206 |
| 2013/0182219 A1* | 7/2013 | Numajiri | A61B 3/113 351/206 |

(Continued)

FOREIGN PATENT DOCUMENTS

| | | |
|---|---|---|
| JP | 2014-068703 A | 4/2014 |
| JP | 2014-068704 A | 4/2014 |

*Primary Examiner* — Mahidere S Sahle
(74) *Attorney, Agent, or Firm* — Venable LLP

(57) ABSTRACT

Provided is an image pickup apparatus including a light beam projecting unit projecting a light beam onto an eye to be inspected, an image signal acquiring unit acquiring an image signal based on the light beam reflected by the eye, a scanning unit included in the light beam projecting unit and scanning the eye with the light beam, an image generating unit generating an image based on the acquired image signal, a position information generating unit arranged outside an optical path of projecting the light beam onto the eye by the light beam projecting unit, a control unit causing the scanning unit to scan the position information generating unit with the light beam, and a correcting unit correcting timing of acquiring the image signal by the image signal acquiring unit based on position information acquired from the light beam with which the position information generating unit is scanned.

13 Claims, 10 Drawing Sheets

(56) References Cited

U.S. PATENT DOCUMENTS

| | | |
|---|---|---|
| 2014/0257076 A1 | 9/2014 | Shimozato |
| 2015/0077710 A1* | 3/2015 | Saito .................... A61B 3/0025 |
| | | 351/221 |
| 2015/0297077 A1 | 10/2015 | Shimozato et al. |
| 2015/0374228 A1* | 12/2015 | Satake .................. G06T 7/0016 |
| | | 351/206 |
| 2017/0119247 A1* | 5/2017 | Walsh .................... A61B 3/102 |

* cited by examiner 301 302 303 304

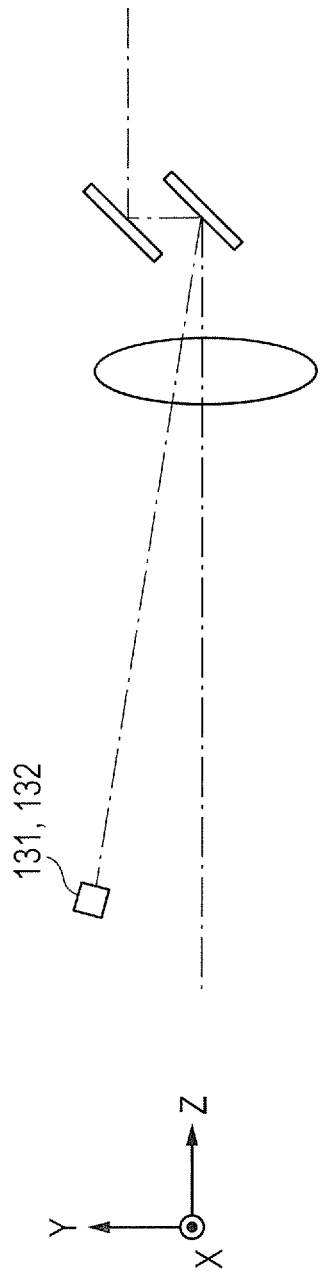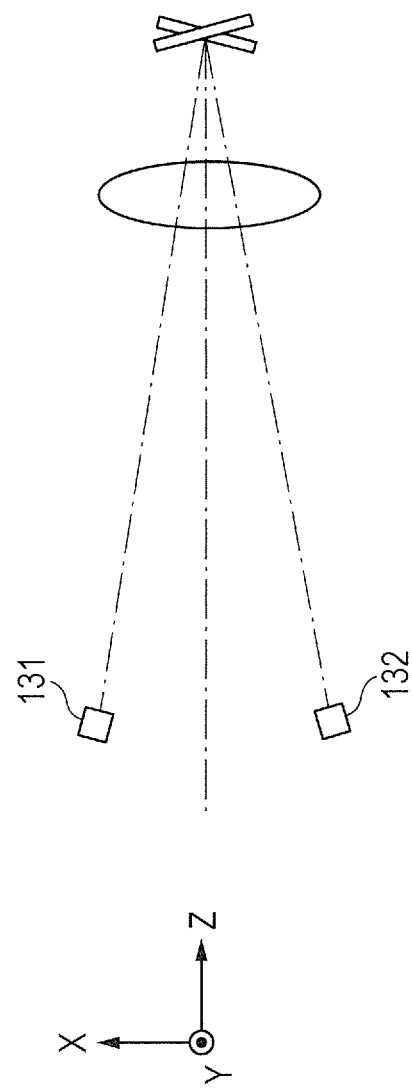

IMAGE PICKUP APPARATUS AND METHOD OF CONTROLLING IMAGE PICKUP APPARATUS

BACKGROUND OF THE INVENTION

Field of the Invention

The present invention relates to an image pickup apparatus configured to pick up an image of an eye to be inspected and a method of controlling the image pickup apparatus.

Description of the Related Art

At present, various ophthalmic image pickup apparatus are used that are configured to scan an eye to be inspected with measuring light and to make an observation and pick up an image using the scanning light that is reflected by the eye to be inspected. Exemplary ophthalmic apparatus include an optical coherence tomography (OCT) system, a scanning laser ophthalmoscope (SLO), and an adaptive optics scanning laser ophthalmoscope (AO-SLO). Those apparatus employ a technology in which a galvano scanner, a resonant scanner, a polygon scanner, or the like is used to scan an eye to be inspected with measuring light so that data at a plurality of points of the eye to be inspected are continuously acquired.

When this technology is used, in order to correctly observe or pick up an image of a desired part of the eye to be inspected, it is necessary to accurately detect a scanning speed and a scanning position of the measuring light on the eye to be inspected in the ophthalmic apparatus. However, it is known that the scanning speed and the scanning position of a scanner used in the ophthalmic image pickup apparatus vary depending on various factors such as individual differences and ambient temperature change.

As a solution to the problem, a technology is known in which a correcting chart is attached at a position conjugate to a light receiving element, and timing of sampling for acquiring a signal from the reflected light is corrected through comparison between a picked-up image of the correcting chart and an image of a fundus (Japanese Patent Application Laid-Open No. 2014-68704). Further, a technology is known in which timing of the sampling is corrected based on a position signal acquired from a drive portion of a resonant scanner (Japanese Patent Application Laid-Open No. 2014-68703).

However, in Japanese Patent Application Laid-Open No. 2014-68704, there is no disclosure of a specific position at which the correcting chart is arranged, and when the correcting chart is attached within an optical axis of an image pickup optical system, it is necessary to attach a new correcting chart every time the data for correction is updated. In this case, there is a problem in that update of the data for correction takes time. In particular, when the scanning speed or the scanning position changes during inspection of an eye and update of the data for correction is attempted for the purpose of identifying the reason for the change, it is often difficult for a user to attach a new correcting chart during the inspection.

Further, the method exemplified in Japanese Patent Application Laid-Open No. 2014-68703 in which a position signal acquired from the drive portion of the resonant scanner is used cannot be applied to a scanner that cannot acquire a position signal. Further, the position signal indicates the position of the scanner alone, and thus, shift of the position of an entire scanner unit in the ophthalmic image pickup apparatus cannot be corrected. In other words, the scanning speed and the scanning position of the measuring light in the ophthalmic image pickup apparatus cannot be accurately corrected.

SUMMARY OF THE INVENTION

The present invention has been made in view of the above-mentioned circumstances, and an object of the present invention is to provide an image pickup apparatus that can accurately correct, in a short time, change in scanning speed and scanning position of measuring light on an object to be inspected, and a method of controlling the image pickup apparatus.

In order to solve the problems described above, according to one embodiment of the present invention, there is provided an image pickup apparatus, including:

a light beam projecting unit configured to project a light beam onto an object to be inspected;

an image signal acquiring unit configured to acquire an image signal based on the light beam reflected by the object to be inspected;

a scanning unit that is included in the light beam projecting unit, and is configured to scan the object to be inspected with the light beam;

an image generating unit configured to generate an image based on the acquired image signal;

a position information generating unit arranged outside an optical path that is formed while the light beam is projected onto the object to be inspected by the light beam projecting unit;

a control unit configured to cause the scanning unit to scan the position information generating unit with the light beam; and a correcting unit configured to correct timing of acquiring the image signal by the image signal acquiring unit based on position information acquired from the light beam with which the position information generating unit is scanned.

According to the present invention, change in scanning speed and scanning position of measuring light on the object to be inspected in the ophthalmic image pickup apparatus can be accurately corrected in a short time.

Further features of the present invention will become apparent from the following description of exemplary embodiments with reference to the attached drawings.

BRIEF DESCRIPTION OF THE DRAWINGS

FIG. 8A is an illustration of a case suitable for assuming operation, and FIG. 8B is an illustration of a case unsuitable for assuming operation.

FIG. 9A and FIG. 9B are explanatory views of photodetectors according to a third embodiment of the present invention seen from different angles.

DESCRIPTION OF THE EMBODIMENTS

Now, exemplary embodiments of the present invention are described with reference to the drawings. Note that, the following embodiments are not intended to limit the present invention defined in the scope of claims, and not all combinations of features described in the embodiments are essential to solving means of the present invention.

Further, in the embodiments, a confocal scanning laser ophthalmoscope (SLO apparatus) is given as an example of an ophthalmic image pickup apparatus, but the present invention is not limited to an SLO apparatus, and is generally applicable to ophthalmic image pickup apparatus configured to scan an eye to be inspected such as an OCT apparatus and an AO-SLO apparatus.

First Embodiment of the Present Invention

An SLO apparatus according to a first embodiment of the present invention is described below.

(Schematic Structure of Apparatus)

Figure 1:
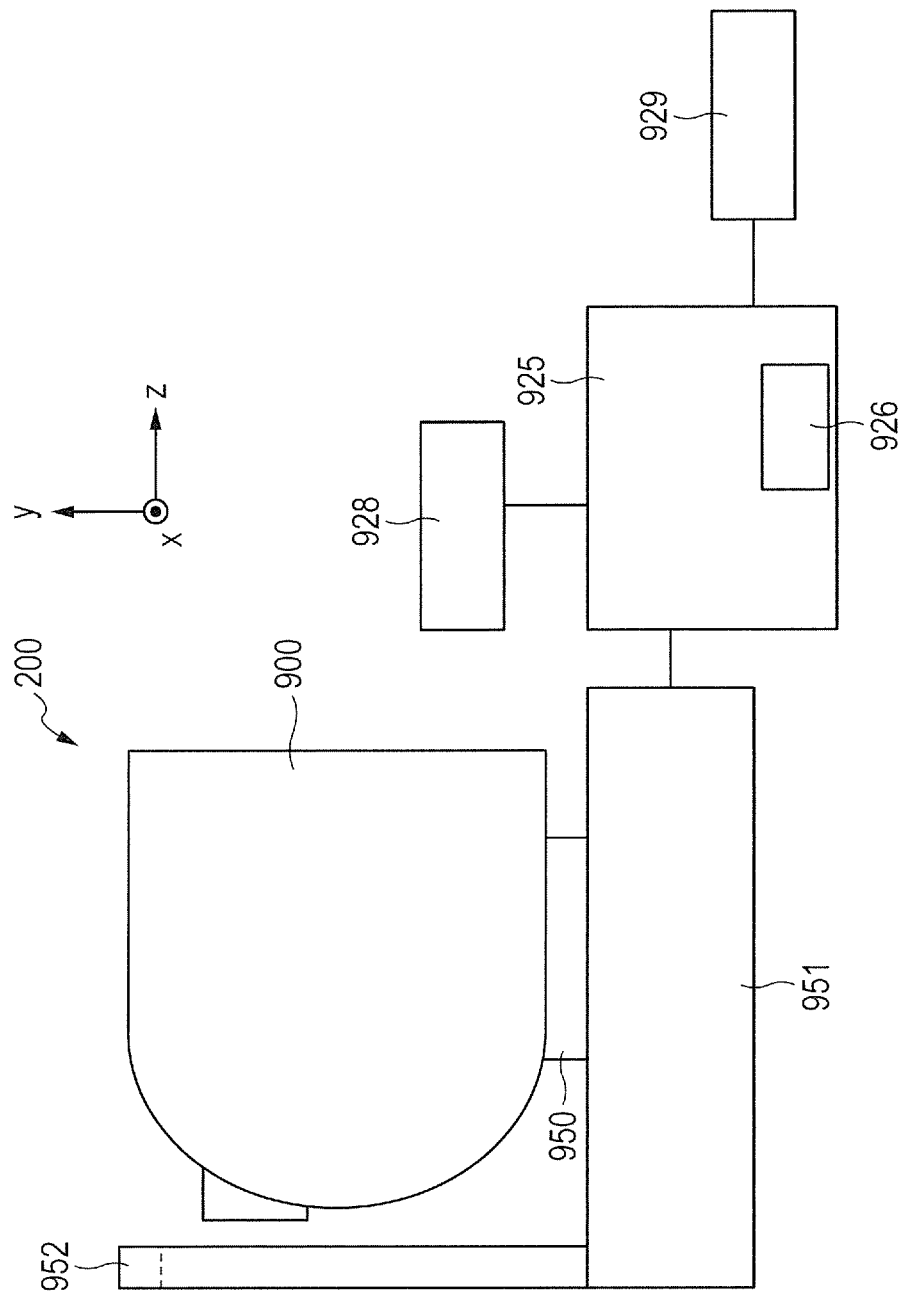
FIG. 1 is a schematic view for illustrating a structure of an entire ophthalmic apparatus according to an embodiment of the present invention.

FIG. 1 is an illustration of a schematic structure of the SLO apparatus according to this embodiment.

An SLO apparatus 200 illustrated in FIG. 1 includes an optical head 900, a stage portion 950, a base portion 951, a chin rest 952, a control portion 925, a memory portion 926, a display portion 928, and an input portion 929. The optical head 900 is a measuring optical system configured to pick up a two-dimensional image of a fundus of an eye to be inspected. The stage portion 950 functions as a moving portion that can move the optical head 900 in x, y, and z directions in FIG. 1 using a motor (not shown). The base portion 951 supports the stage portion 950 and houses therein a power supply, part of the optical system, and the like. The chin rest 952 is fixed to the base portion 951 and promotes fixation of an eye of a subject (eye to be inspected) through fixation of the chin and the forehead of the subject.

The control portion 925 is a personal computer that also serves as a control portion of an optical tomographic image pickup apparatus, and is configured to not only control the SLO apparatus but also perform other operations such as the configuration of a fundus image. The memory portion 926 includes a hard disk configured to store therein a program for picking up a fundus image and the like, and is built into the control portion 925. The display portion 928 is a monitor. The input portion 929 gives instructions to the personal computer, and, specifically, includes a keyboard and a mouse. In this embodiment, the control portion (personal computer), the hard disk, the display portion, and the input portion are arranged outside the SLO apparatus 200, but may also be built into the SLO apparatus 200.

(Structure of Image Pickup Optical System)

Next, a structure of an image pickup optical system of the ophthalmic image pickup apparatus according to this embodiment is described with reference to FIG. 2.

First, the inside of the optical head 900 is described. In the optical head 900, an objective lens 101-1 is arranged so as to be opposed to an eye 100 to be inspected. A first dichroic mirror 102 is arranged on an optical axis of the objective lens 101-1. The optical path leading to the eye 100 to be inspected is split by the first dichroic mirror 102 into an optical path L1 of an anterior ocular segment observing system and an optical path L2 of an internal fixation lamp and an SLO optical system, depending on the respective wavelength bands thereof.

The optical path L1 is formed to cause light reflected from the fundus to be received by a CCD 172 for observing the fundus, and a lens 122 and a lens 123 are arranged on an optical axis thereof. The CCD 172 has sensitivity to a wavelength of illumination light for observing an anterior ocular segment (not shown). specifically, to a wavelength of approximately 970 nm.

A second dichroic mirror 106 is arranged on an optical axis of the optical path L2. The optical path L2 of light reflected from the fundus of the eye 100 to be inspected is split by the second dichroic mirror 106 into an optical path L3 of the internal fixation lamp optical system and an optical path L4 of the SLO optical system. A lens 101-2, a galvano scanner 104, a resonant scanner 103, and a lens 105 are arranged on the optical path L2 from the first dichroic mirror 102 side in this order, and the optical path L2 leads to the second dichroic mirror 106.

An SLO focus lens 107, a perforated mirror 108, an SLO light source 109, and a photodetector 110 are arranged on an optical axis of the SLO optical system in a transmitting direction of the second dichroic mirror 106. The photodetector 110 forms a light receiving unit configured to receive light that is projected onto the eye 100 to be inspected and is reflected from the eye 100 to be inspected according to this embodiment. Further, a fixation focus lens 111 and an internal fixation lamp 112 are arranged on an optical axis of the internal fixation lamp optical system in a reflecting direction of the second dichroic mirror 106. Further, the photodetector 110 is connected to an A/D converter 140. Further, the A/D converter 140 is connected to an FPGA 150. The photodetector 110 produces an output depending on received light, and the A/D converter 140 converts the output of the photodetector 110 into a digital signal. The FPGA 150 samples output of the A/D converter 140 at predetermined sampling intervals, and outputs the sampled digital signal to the control portion 925. The control portion 925 generates and controls display of an image of the eye to be inspected based on the output from the FPGA 150. In this embodiment, a method of correcting the intervals of the sampling by the FPGA 150 is described, but intervals of sampling by the A/D converter 140 (intervals of A/D conversion) may also be changed. The control portion 925 may also perform sampling at predetermined sampling intervals. Further, the FPGA 150 may be included in the control portion 925.

The SLO light source 109 emits measuring light having a center value near a wavelength of 780 nm. The photodetector 110 has sensitivity to received light having a wavelength of approximately 780 nm. Meanwhile, the internal fixation lamp 112 emits visible light to promote visual fixation of the subject.

Each of a light beam emitted from the SLO light source 109 and a light beam emitted from the internal fixation lamp 112 forms an image once in the vicinity of the first dichroic mirror 102, and forms an image again in the vicinity of the fundus of the eye 100 to be inspected. The SLO focus lens 107 and the fixation focus lens 111 are driven along the optical axis by a motor (not shown) so that the positions of the images formed in the second formation match with a plane of the fundus of the eye 100 to be inspected. Through drive of those focus lenses, the positions of the images formed in the first formation also change in the vicinity of the first dichroic mirror 102.

The position of an image formed of a light beam on the fundus is changed by the resonant scanner 103 configured to drive the light beam in the X direction and the galvano scanner 104 configured to drive the light beam in the Y direction. The scanners cause the light beam to two-dimensionally scan the fundus. The light beam scatters on the fundus. Reflected light scattered in a direction of the optical path L2 is reflected by the perforated mirror 108 to be detected by the photodetector 110. The photodetector 110 is, for example, a photodiode, and forms an image signal acquiring unit according to this embodiment. The light beam emitted from the SLO light source 109 and the resonant scanner 103 described here form the measuring light and a scanning unit configured to scan with the measuring light, respectively, according to this embodiment. Further, the photodetector 110 forms a first acquiring unit configured to acquire an image signal based on return light of the measuring light from the eye 100 to be inspected.

Through processing a signal acquired by the photodetector 110 in a method described below, an SLO image is acquired. In this way, the SLO apparatus 200 can pick up an image in an entire region of interest of the fundus of the eye to be inspected. The structure from the eye 100 to be inspected to the SLO optical system and the SLO optical system described above form a light beam projecting unit configured to project a light beam onto the eye 100 to be inspected in this embodiment. Further, the resonant scanner 103 and the galvano scanner 104 form a scanning unit included in the light beam projecting unit and configured to scan the eye to be inspected with the light beam in this embodiment.

Further, through controlling lighting of the internal fixation lamp 112 in synchronization with scanning with the resonant scanner 103 and the galvano scanner 104, various patterns such as a cross-shaped pattern or an x-shaped pattern can be projected onto various positions of the fundus of the eye to be inspected. This enables directing the eye to be inspected in various directions, and an image of a wide region in the fundus of the eye to be inspected can be picked up.

A chart 130 arranged at a position off the optical axis of the optical path L2 is a scan-correcting chart described below. As illustrated in FIG. 2, the scan-correcting chart 130 is arranged off the optical axis of the optical path L2. In the case illustrated in FIG. 2, the scan-correcting chart 130 is arranged in parallel with the optical axis of the optical path L2, but the present invention is not limited thereto. The scan-correcting chart 130 may be arranged so as to be tilted against the optical axis of the optical path L2. For example, the scan-correcting chart 130 may be arranged so as to be perpendicular to the optical axis of the optical path L2, or may be arranged so as to be tilted against the optical axis of the optical path L2.

(Generation of SLO Image)

Figure 3A:
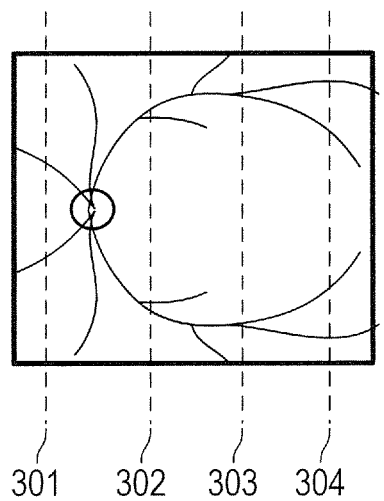
FIG. 3A is an illustration of an SLO image acquired by the ophthalmic apparatus.

Next, the SLO image is described with reference to FIG. 3A and FIG. 3B.

A signal level acquired by the photodetector 110 is converted to brightness of each pixel, and the SLO image is generated. The actual SLO image is generated by a module configured to function as an image generating unit in the control portion 925. Specifically, pixels acquired while the resonant scanner 103 scans the fundus once with the light beam in the X direction are arranged in a horizontal direction to acquire one-line data. Pieces of one-line data acquired through repeating the acquisition are arranged in a vertical direction to acquire a two-dimensional image as illustrated in FIG. 3A. The resonant scanner 103 is driven to reciprocate, and thus, scanning at odd-numbered times and scanning at even-numbered times are in opposite directions. Therefore, in FIG. 3A, through arranging data in odd-numbered lines and data in even-numbered lines in opposite directions, a two-dimensional image with a unified direction is acquired.

Figure 3B:
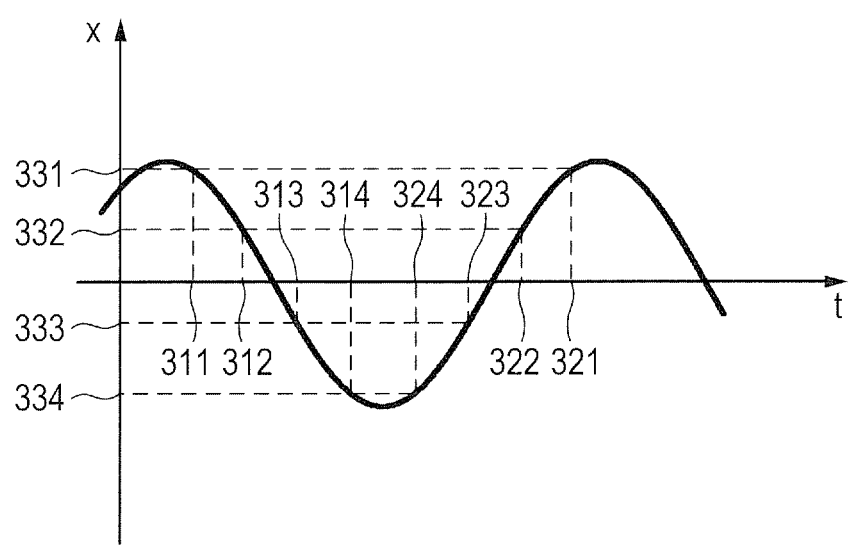
FIG. 3B is an explanatory view of relationship between the SLO image illustrated in FIG. 3A and operation of a resonant scanner.

FIG. 3B is an illustration of how the resonant scanner 103 is driven. The horizontal axis denotes time, while the vertical axis denotes angle of oscillation of the resonant scanner 103. A pixel on a dotted line 301 in FIG. 3A is formed from a signal at Time 311 or 321 in FIG. 3B. Similarly, pixels on dotted lines 302, 303, and 304 are formed from signals at Times 312 or 322, Times 313 or 323, and Times 314 or 324, respectively. In this case, the Times 311, 312, 313, and 314 are at equal time intervals. Further, Times 321, 322, 323, and 324 are at equal time intervals. The angles of oscillation of the resonant scanner 103 at those times are 331, 332, 333, and 334, respectively.

The resonant scanner 103 is not driven with constant speed, and thus, the intervals between the angles 331, 332, 333, and 334 at the respective times are different from each other. Therefore, the intervals between the dotted lines 301, 302, 303, and 304 in FIG. 3A are not actually equal on the fundus, but are illustrated as equal intervals in FIG. 3A. In other words, the SLO image illustrated in FIG. 3A is distorted. Therefore, the intervals between signal acquisition by the photodetector 110 are required to be corrected by a method described below.

(Description of Scan-Correcting Chart)

The scan-correcting chart 130 is described with reference to FIG. 4A to FIG. 4C.

Figure 2:
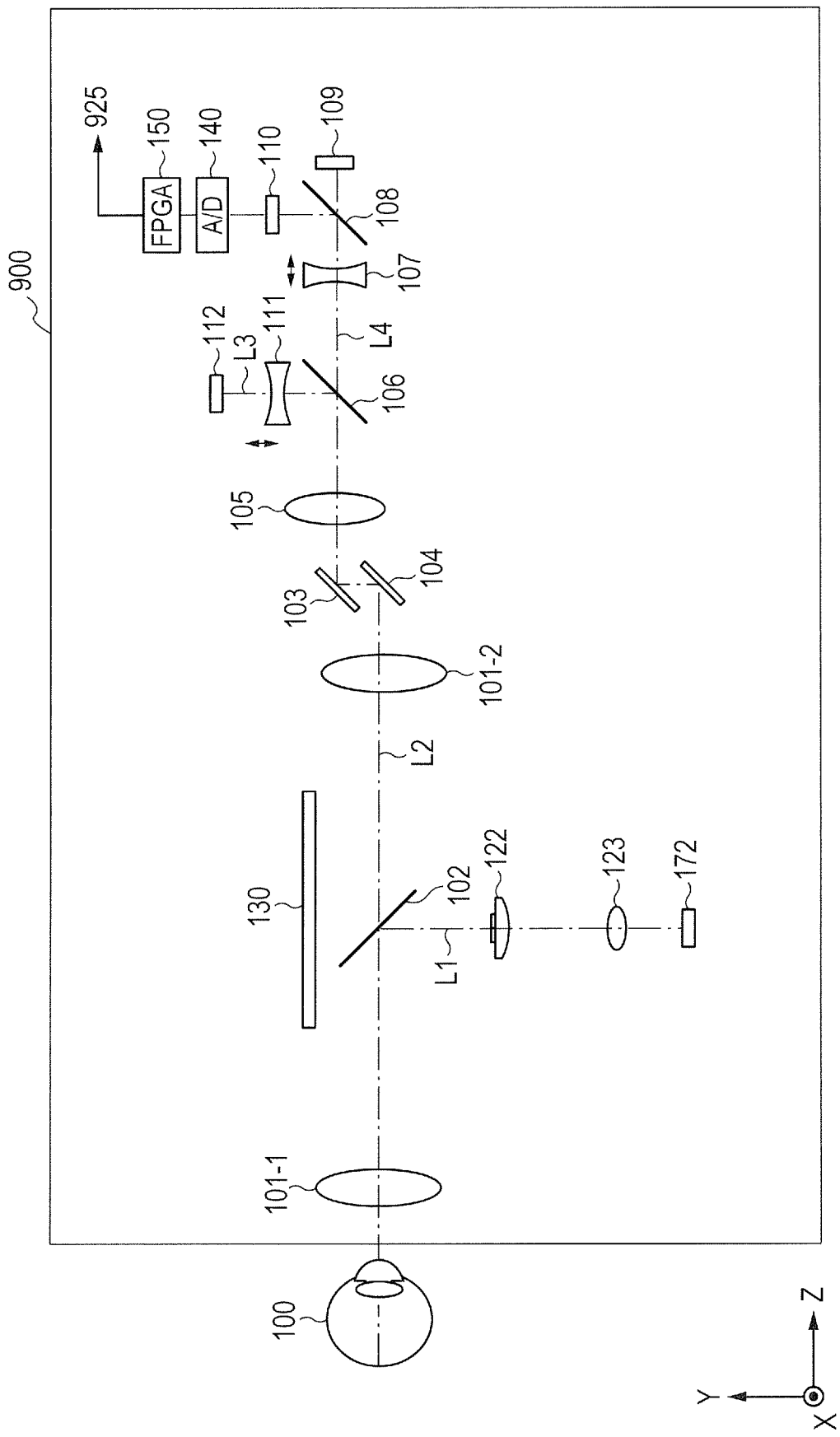
FIG. 2 is an explanatory view of an optical system in the ophthalmic apparatus illustrated in FIG. 1.
Figure 4A:
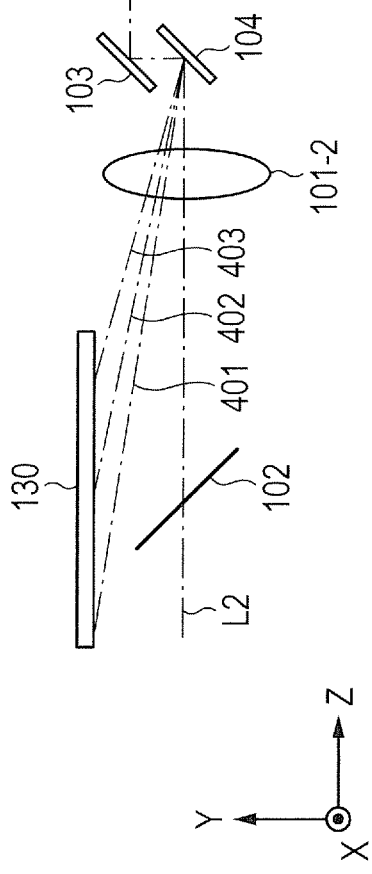
FIG. 4A is an enlarged view of a scan-correcting chart and related portions according to a first embodiment of the present invention.

FIG. 4A is an illustration of a portion related to the scan-correcting chart 130 illustrated in FIG. 2. In correction, the galvano scanner 104 changes an angle of a mirror portion, and projects the light beam onto the scan-correcting chart 130 arranged off the optical axis along, for example, an optical path 401. Through changing the angle of the mirror portion of the galvano scanner 104, the light beam can be guided along different optical paths such as an optical path 402 or an optical path 403 to be projected onto an arbitrary position on the scan-correcting chart 130. The scan-correcting chart 130 is arranged in the vicinity of the first dichroic mirror 102, that is, at a position at which the light beam forms an image. Therefore, the light beam emitted from the SLO light source 109 focuses on any one of positions on the scan-correcting chart 130. The position at which the light beam forms an image depends on the position of the SLO focus lens 107 on the optical axis. Therefore, through controlling the angle of the galvano scanner 104 depending on the position of the SLO focus lens 107, the light beam can focus on the scan-correcting chart 130. In other words, the scan-correcting chart 130 is arranged at a position which is outside the scanned area by the light beam when the fundus of the eye to be inspected is scanned with the light beam and on which the light beam can focus with a focusing unit for light for correction including the SLO focus lens 107 and the galvano scanner 104. Further, the position can be defined as a predetermined range around a position at which, when the light beam forms an image on an inspection position of the eye to be inspected, an image is formed between the resonant scanner 103 and the inspection position of the eye to be inspected, that is, a range in which the image formation position can be adjusted with the focusing unit for light for correction.

Figure 4C:
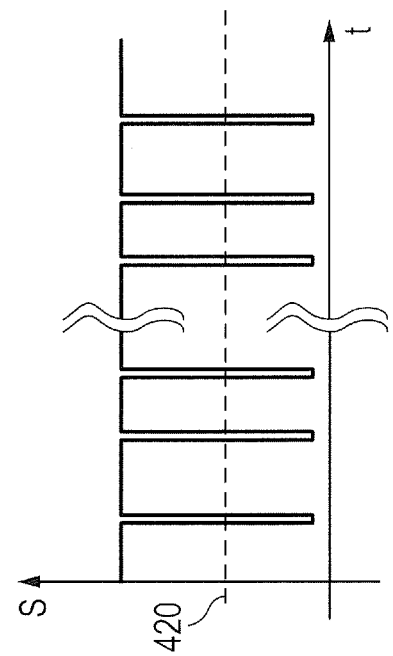
FIG. 4C is an explanatory view of signals acquired from the scan-correcting chart.
Figure 4B:
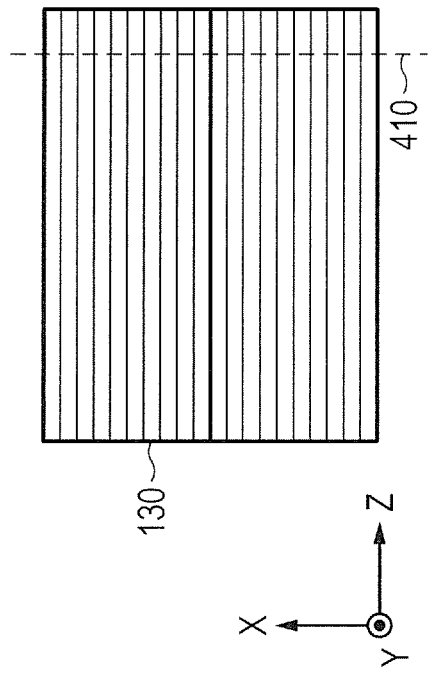
FIG. 4B is an illustration of the scan-correcting chart.

FIG. 4B is an illustration of a chart surface of the scan-correcting chart 130. A case in which the scan-correcting chart 130 is seen from a direction of the first dichroic mirror 102 in FIG. 4A is illustrated in FIG. 4B. On the chart surface of the scan-correcting chart 130, a plurality of parallel lines having a low reflectivity are drawn in parallel with a scanning direction of the galvano scanner 104 on a Lambertian surface having a high reflectivity. Further, in this embodiment, a center line is thicker than other lines.

In this case, the light beam is projected onto a position depending on the angles of the resonant scanner 103 and the galvano scanner 104. For example, when the galvano scanner 104 is at an angle at which the light beam is projected along the optical path 403, the light beam is projected at any one of positions on a scanning line 410. Which of the positions on the scanning line 410 the light beam is projected onto depends on the angle of the resonant scanner 103. In particular, when the angle of the resonant scanner 103 is at the center, the light beam is projected onto a point at which the scanning line 410 and the thick line at the center of the scan-correcting chart 130 intersect each other. Through driving the resonant scanner 103 in this state, the scan-correcting chart 130 can be scanned with the light beam along the scanning line 410. The parallel lines on the scan-correcting chart 130 are drawn at positions corresponding to equiangular angles of the resonant scanner 103, respectively.

FIG. 4C is a graph for showing strength of signals acquired through scanning of the scan-correcting chart 130 with the light beam described above. In FIG. 4C, the horizontal axis denotes time, while the vertical axis denotes signal strength. The reflectivity is low on the parallel lines on the scan-correcting chart 130, and thus, the signal strength is low while the lines are scanned. Through binarizing the signal strength data with a threshold value thereof, which is represented by 420, time during which the lines are scanned and time during which the lines are not scanned can be discriminated from each other. Further, as described above, according to this embodiment, among the parallel lines, the center line is thicker than other lines. This increases time during which the strength of signals acquired while the center line is scanned with the light beam is low compared with cases of other lines, and thus, a reference position on the scan-correcting chart 130 scanned with the light beam is acquired. In this embodiment, the thickness of the lines is changed, but the present invention is not limited thereto. It is enough that signal change is acquired through change in interval, change in reflectivity, or the like so that the center line is discriminated from other lines.

It is enough that the scan-correcting chart 130 described above is a chart-like structure having thereon a diffuse surface and regions having a reflectivity different from the reflectivity of the diffuse surface and arranged in parallel with one another, the diffuse surface and the regions being arranged in accordance with a predetermined rule. In this embodiment, the regions arranged in parallel with one another are linear regions extending in a direction parallel with any one of the X direction and the Y direction in which the scanning unit scans with the light beam. More specifically, it is preferred that the linear regions be arranged in parallel with the scanning direction of the galvano scanner 104. In other words, it is preferred that the linear regions be arranged perpendicularly to the scanning direction of the resonant scanner 103. Further, it is preferred that the chart-like structure be, as described in this embodiment and illustrated in FIG. 2, arranged outside the optical path that is formed while the light beam projecting unit projects the light beam onto the eye to be inspected. Further, it is preferred that the scan-correcting chart 130 be arranged between the objective lens 101-1 and the resonant scanner 103. That is, the scan-correction chart 130 may be a member having a pattern located outside the scanned area of the measuring light for the eye to be inspected and within an area on which the measuring light can be projected by the resonant scanner 103.

(Flow of SLO Photographing)

Figure 5:
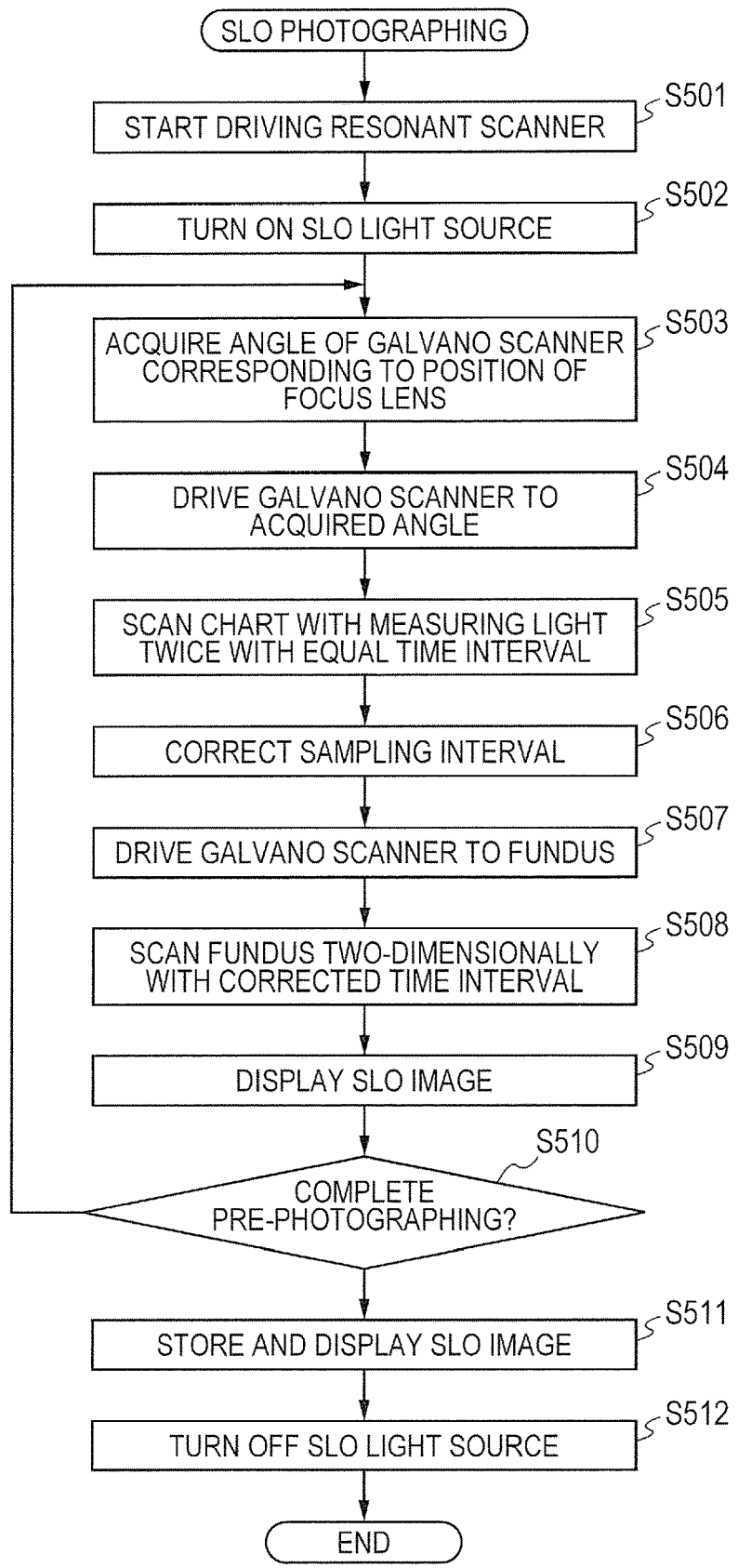
FIG. 5 is a flow chart for illustrating photographing steps to acquire the SLO image according to the embodiment of the present invention.

FIG. 5 is a flow chart for illustrating the flow of SLO photographing. First, in Step S501, the control portion 925 starts driving the resonant scanner 103. Then, in Step S502, the control portion 925 turns on the SLO light source 109. Next, in Step S503, the control portion 925 acquires the angle of the galvano scanner 104 corresponding to the position of the SLO focus lens 107 on the optical axis. The corresponding angle is an angle at which the light beam focuses on the scan-correcting chart 130 in the current state of the SLO apparatus 200, and is calculated by the control portion 925 based on the optical system. The angle may be determined not through calculation but based on a table stored in advance.

Then, in Step S504, the control portion 925 drives the galvano scanner 104 to the angle determined in the manner described above. After the driving of the galvano scanner 104 ends, in Step S505, the resonant scanner 103 scans the scan-correcting chart 130 with the light beam. The control portion 925 functions as a control unit configured to cause the resonant scanner 103 serving as the scanning unit to scan the scan-correcting chart 130 with the light beam. At this time, signal acquisition (sampling) by the FPGA 150 is performed at equal time intervals determined in advance. Through driving the resonant scanner 103 to reciprocate in this way, two pieces of one-line data are acquired. That is, the measuring light is scanned on the scan-correcting chart 130 with plural times. So-called positional information relating to the scanning position can be obtained by scanning the light on the scan-correcting chart 130 by the resonant scanner 103. Specifically, the control portion 925 causes the resonant scanner 103 to scan the scan-correcting chart 130 a plurality of times, which includes reciprocating scanning, so that a plurality of pieces of position information (information indicating operation of the scanning unit) are acquired. The number of pieces of one-line data to be acquired may be more than two.

Then, in Step S506, the control portion 925 corrects intervals of the sampling by the FPGA 150 by a correcting method described below. Then, in Step S507, the control portion 925 drives the galvano scanner 104 toward the fundus. Next, in Step S508, the control portion 925 two-dimensionally scans the fundus with light beams using the resonant scanner 103 and the galvano scanner 104. It is preferred that the scanning with the measuring light for the purpose of acquiring image information, the scanning with the measuring light for the purpose of acquiring data for correction, and the correction of the sampling intervals described above be performed in series. At this time, signal acquisition by the photodetector 110 is performed at the intervals corrected in Step S506.

In other words, the image is generated in accordance with information acquired by reflected light corresponding to the scanning position with the light beam using both the scanners or the scanning position corresponding to the angle positions of the scanners. At that time, the method of generating an image by the image generating unit is corrected based on the information acquired through scanning the scan-correcting chart 130 with the light beam. More specifically, the timing of sampling the output of the photodetector 110 by the FPGA 150 described above is corrected. In other words, the timing of acquiring the image information obtained when the image signal based on light reflected from the eye 100 to be inspected is acquired is corrected. The acquisition timing is corrected by a module that functions as a correcting unit in the control portion 925. Through the correction, the sampling timing at equal time intervals is changed to that at unequal time intervals so that the positions at which the light beam is reflected on the eye 100 to be inspected, from which the image signal is acquired, is at equal intervals.

In this way, in Step S509, the control portion 925 generates the SLO image and displays the SLO image on the display portion 928. In Step S510, the control portion 925 determines whether or not pre-photographing is completed. When there is input in the form of pressing down a photographing button from the input portion 929, the control portion 925 determines that the pre-photographing is completed. The determination criterion is not limited thereto. For example, whether or not the state is a focusing state may be determined from the brightness of the SLO image and the focusing state may be regarded as meaning that the pre-photographing is completed. Further, an arrangement for acquiring an information designating the operation of the resonant scanner 103 by using the san-correcting chart 130 and the like forms a second acquiring unit.

When it is determined that the pre-photographing is completed, in Step S511, the control portion 925 stores the SLO image in the memory portion (hard disk) 926, and displays the SLO image on the display portion 928. Finally, in Step S512, the control portion 925 turns off the SLO light source 109, and the photographing ends.

When it is determined that the pre-photographing is not completed, the process returns to Step S503, and the control portion 925 repeats the processing described above. While the processing described above is repeated, an operator can drive the SLO focus lens 107 through input from the input portion 929 to focus the light beam on the fundus. Alternatively, the control portion 925 may periodically determine whether or not the state is the focusing state in the method described above and may drive the SLO focus lens 107 so that the light beam may focus on the fundus.

Through performing correction and image acquisition in series in this way, the control portion 925 can correct the sampling intervals every time an SLO image is acquired. Therefore, even when time taken by the resonant scanner 103 to scan changes with time, a correction can be made promptly. The control portion 925 may correct the sampling intervals not every time an SLO image is acquired but every time N (N is 2 or more) SLO images are acquired or after scanning the measuring beam. That is, the step of acquiring the image signal of the SLO images, the step of acquiring the information designating the operation of the resonant scanner 103, and the step of determining the acquiring timing of the image signal based on the information designating the operation may be repeatedly performed.

The flow of the SLO photographing is described above. The timing of making a correction may be controlled by other methods. For example, the correction may be made every time a predetermined time elapses, or the correction may be made before the inspection starts. When change in resonant scanner is large, the correction may be made while an image is acquired. The methods may be switched through controlling drive of the galvano scanner.

(Description of Correction of Scanning)

Figure 6:
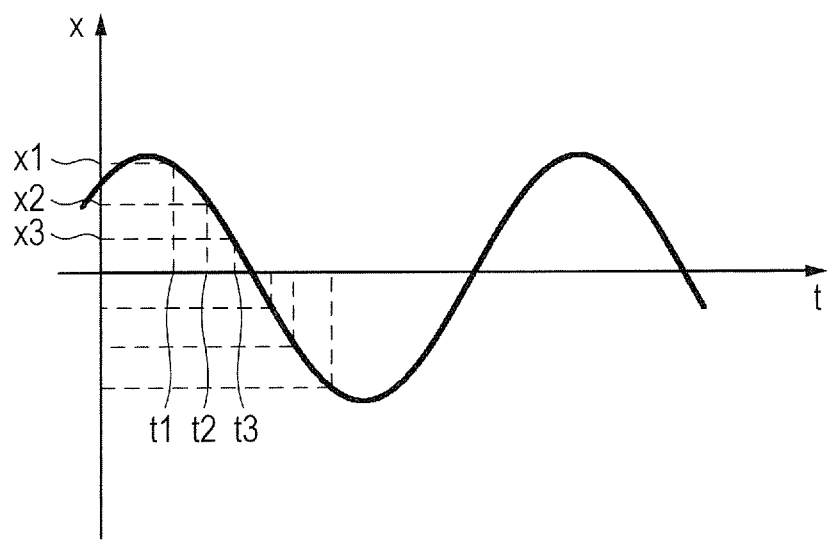
FIG. 6 is an explanatory view of a method of correcting scanning according to the first embodiment of the present invention.

Next, a method of correcting the scanning is described with reference to FIG. 6. The scanning is corrected with regard to a forward path and a return path of the reciprocated operation of the resonant scanner 103. The forward path and the return path are different only in that the direction of operation is opposite, and thus, only correction in the forward path is described below.

Data on strength of signals acquired from the scan-correcting chart 130 in Step S505, for example, the data illustrated in FIG. 4C, is binarized with a threshold value thereof, which is represented by 420, and the barycenter thereof is calculated. Through the calculation, detected times t1, t2, and t3 are acquired for the respective lines. Description of the fourth and subsequent lines is omitted. The angles of the resonant scanner 103 corresponding to the respective lines on the scan-correcting chart 130 are stored in advance in the memory portion 926, from which angles x1, x2, and x3 of the resonant scanner at the times t1, t2, and t3 are acquired. Points (t1, x1), (t2, x2), (t3, x3), and all the rest of the points determined similarly are plotted in a coordinate system in which the horizontal axis denotes time t while the vertical axis denotes angle x of the resonant scanner 103, to thereby acquire a graph of FIG. 6. The angle x of the resonant scanner 103 is represented by, for example, coordinates in a coordinate system with the optical axis of the resonant scanner having a coordinate of 0. For example, a center of the angle of the oscillation range of the resonant scanner 103, which changes when acquiring the SLO image, is at 0 degrees.

Further, the resonant scanner 103 outputs a synchronizing signal every period, and thus, through detecting the synchronizing signal, the control portion 925 can calculate the period of the resonant scanner 103. The period is represented by T.

Then, the entire data described above can be approximated by Expression (1):

$$x = A\cos(\omega t + \alpha) \qquad (1)$$

where A is an amplitude, that is, the maximum angle of oscillation of the resonant scanner 103, $\omega$ is an angular frequency (=$2\pi/T$), and $\alpha$ is an initial phase, that is, a phase at a time at which a synchronizing signal of the resonant scanner is detected. Expression (1) can be transformed into Expression (2) below:

$$x = a\sin(\omega t) + b\cos(\omega t) \qquad (2)$$

where $$A = \sqrt{a^2 + b^2} \quad \sin(\alpha) = -\frac{a}{\sqrt{a^2 + b^2}} \quad \cos(\alpha) = \frac{b}{\sqrt{a^2 + b^2}} \qquad (3)$$

is satisfied.

In Expression (2), a and b can be determined by least squares from the data (t1, x1), (t2, x2), (t2, x2) . . . described above. Then, A and $\alpha$ can be determined using Expression (3).

The number of pixels in the SLO image is represented by n, and the angles of the resonant scanner corresponding to the observation range on the fundus are represented by from X1 to Xn. In order to acquire signals through scanning the fundus at equal intervals, signals may be acquired at coordinates acquired by Expression (4) below:

$$X_i = \frac{(n-i)X_1 + (i-1)X_n}{n-1} \quad (4)$$

where i is the number of the pixel, that is, an integer from 1 to n.

Substituting X1, X2, X3, . . . , and Xn into an inverse function of Expression (1) acquires times T1, T2, . . . , and Tn at which the signals are to be acquired. T1, T2, . . . , and Tn are stored in the memory portion 926 as corrected signal acquisition times. In Step S508, signals are acquired at those times to enable acquisition of an SLO image without or with only a small amount of distortion.

The method of correcting the signal acquiring interval at a time of obtaining the signal by scanning the measuring light is described above. In this correcting method, not only drive of the resonant scanner is corrected alone but the entire SLO optical system can be corrected taking change in positional relationship among the SLO light source, the resonant scanner, the mirrors, and the like into consideration. Therefore, the scanning position of the SLO apparatus can be accurately corrected.

The arrangement (position or angle) of the scan-correcting chart 130 may be different from that illustrated in FIG. 4A and the like. The chart may be shorter with the angle of the galvano scanner in the correction being controlled to a predetermined fixed angle. In that case, depending on the position of the SLO focus lens 107, the light beam may not focus on the chart, and thus, control may be performed so that, in the correction, the SLO focus lens 107 may be driven to a certain position. Alternatively, a signal may be acquired in an unfocused state and the position of a line on the chart may be detected through determining the barycenter of a portion having low signal strength.

Further, in this embodiment, the times T1, . . . , and Tn at which signals are to be acquired are determined in advance, and after that, the signals are acquired, but signals may be acquired first. For example, signals may be acquired at all times at which the acquisition is possible, and the acquired signal levels may be stored. After that, data corresponding to T1, . . . , and Tn may be selected.

As described above, the chart-like structure illustrated as the scan-correcting chart in the embodiment described above is used for acquiring position information relating to the scanning position obtained when the scanners perform scanning with the light beam. Therefore, those structures are defined as a position information generating unit according to the present invention.

Second Embodiment of the Present Invention

According to a second embodiment of the present invention, instead of the scan-correcting chart, a photodetector is used as the position information generating unit, and the signal acquisition time is corrected based on a time at which the photodetector receives light.

(Structure of Apparatus)

Figure 7A:
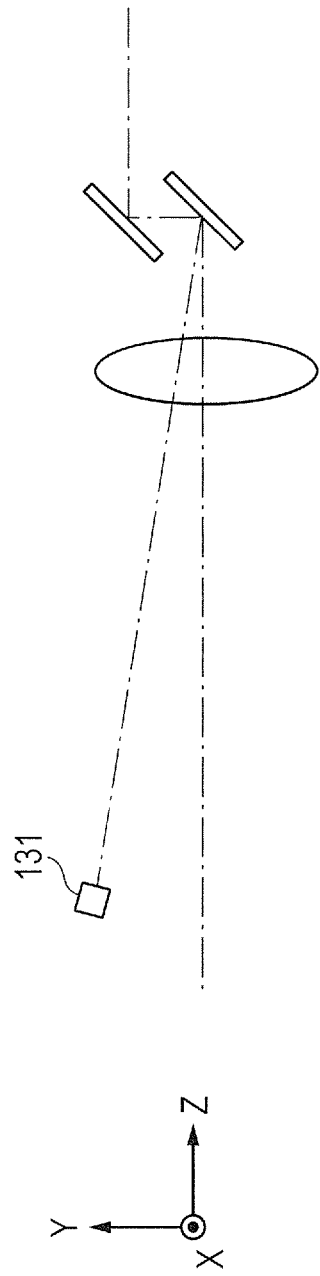
FIG. 7A and FIG. 7B are explanatory views of a photodetector according to a second embodiment of the present invention seen from different angles.
Figure 7B:
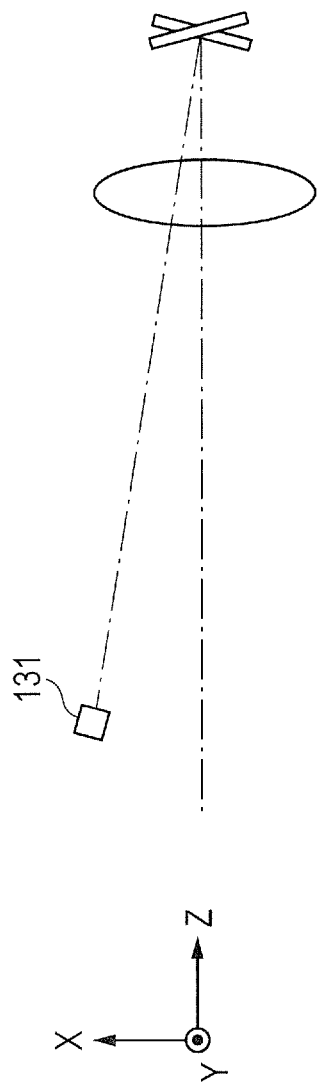

FIG. 7A and FIG. 7B are illustrations of arrangement of the photodetector according to this embodiment. The structure of the apparatus according to this embodiment is similar to that in the first embodiment except for the portion illustrated in FIG. 7A and FIG. 7B.

A photodetector 131 has sensitivity to the vicinity of the wavelength of light emitted from the SLO light source, and is arranged at a position close to the position at which the scan-correcting chart is arranged in the first embodiment. FIG. 7A is an illustration of the photodetector 131 and a related structure observed from an angle that is the same as that in FIG. 4A referred to in the first embodiment. The photodetector 131 is arranged outside the optical path that is formed while the light beam projecting unit projects the light beam onto the eye to be inspected.

Further, the photodetector 131 is arranged at a position away from the center of the scanned area of measuring light scanned by the resonant scanner 103, in a direction of driving the resonant scanner, that is, of the X axis. FIG. 7B is an illustration of the arrangement of the photodetector 131 observed from an angle different from that in FIG. 7A. The reason that the photodetector 131 is not arranged at the center of the scanned area on the X axis is described below.

When the resonant scanner scans a sensor surface of the photodetector 131, the photodetector 131 detects light from the SLO light source, and outputs an analog signal. The analog signal is binarized by a comparator at a certain threshold value, and is input to the control portion 925 as a pulse-shaped digital signal. A time at the center of the pulse at this time is defined as a detected time. The detected time may be defined otherwise. For example, for the purpose of suppressing influence of noise on the analog signal, a threshold value for a rising edge and a threshold value for a falling edge of the pulse signal may be separately prepared. Further, the barycenter of the analog signal may be determined to be used as the detected time. Alternatively, a special computational expression in accordance with the output characteristics of the photodetector and the drive characteristics of the resonant scanner may be used to define the detected time.

(Description of Correction of Scanning)

In correction of the scanning according to this embodiment, Expression (1) in the first embodiment is used in a different way from that in the first embodiment to assume the operation of the resonant scanner. The assuming method is described with reference to FIG. 8A and FIG. 8B.

Figure 8A:
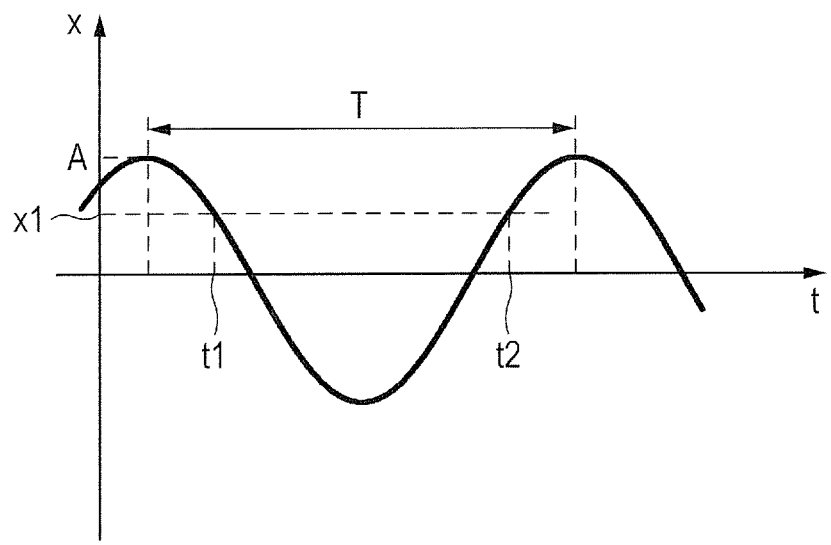
FIG. 8A and FIG. 8B are explanatory views of a method of correcting scanning according to the second embodiment of the present invention.

FIG. 8A is an illustration of the timing of driving the resonant scanner and detecting by the photodetector according to this embodiment. When the resonant scanner reciprocates once, the photodetector 131 detects light from the SLO light source once in the forward path and once in the return path. A detected time in the forward path is represented by t1, a detected time in the return path is represented by t2, and an angle of the resonant scanner in scanning the photodetector is represented by x1. The angle x1 is a constant determined when the apparatus is adjusted.

Through solving two equations in which (t1, x1) and (t2, x1), respectively, are substituted for (t, x) in Expression (1), A and α in Expression (1) can be determined. Specifically, the following can be acquired.

$$\alpha = \pi - \frac{\omega(t_1 + t_2)}{2} \quad (5)$$

$$A = -\frac{x_1}{\cos\left(\frac{\omega(t_2 - t_1)}{2}\right)} \quad (6)$$

After that, similarly to the first embodiment, coordinates X1, X2, X3, . . . at which signals are to be acquired are determined using Expression (4). Through substituting the coordinates in Expression (1), the times T1, T2, . . . , and Tn at which the signals are to be acquired can be acquired.

Figure 8B:
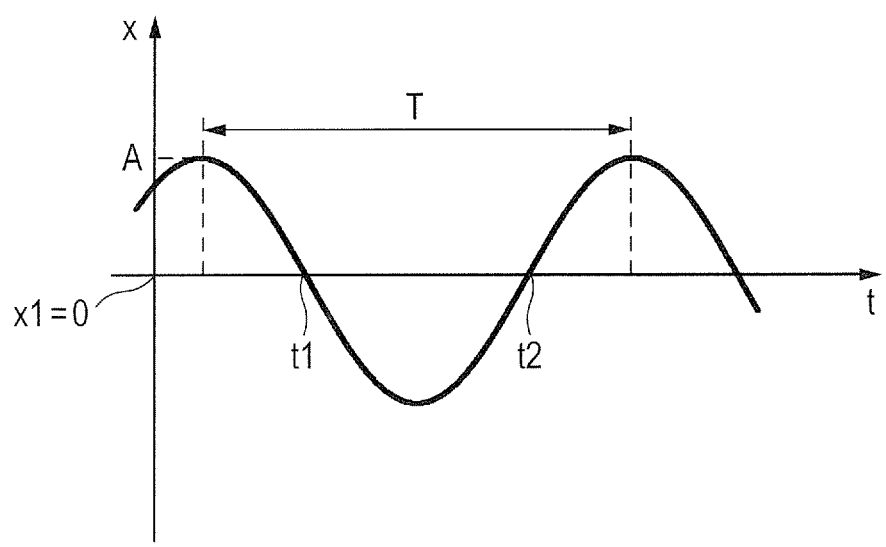

FIG. 8B is an illustration of a case in which, differently from this embodiment, the photodetector is arranged at the center of the scanned area on the X axis. In this case, the amplitude of the resonant scanner, that is, A in Expression (1) cannot be determined, which is described below. As can be seen from FIG. 8B, when x1 is at the center, that is, when x1 is 0, time from the detected time t1 to the detected time t2 is exactly one half of a period T, that is, T/2 (=π/ω). If t2−t1=π/ω and x1=0 are substituted in Expression (6), then A=−0/0, and thus, A cannot be determined. Therefore, the photodetector 131 is required to be arranged at a position away from the center of the X axis. Meanwhile, at a position away from the center, change in speed of the resonant scanner is large, and thus, the detection accuracy, that is, the accuracy of the detected time at the center of the pulse may be reduced. Further, depending on the position, the extent of the oscillation of the resonant scanner may be too small to scan the photodetector 131. Therefore, it is desired that the photodetector 131 be arranged at a position close to a position at which the extent of the oscillation of the resonant scanner is approximately a half of the maximum extent. It is preferable that the photodetector 131 of the light receiving unit is arranged at a position away from a scanning center of the area scanned by the resonant scanner 103 with measuring light, by a predetermined distance.

Further, according to this embodiment, the period of the resonant scanner is calculated from synchronizing signals of the resonant scanner, but other methods may be used. For example, the period of the resonant scanner may be calculated based on detected times by a sensor. At that time, taking into consideration the possibility that the resonant scanner may be driven to reciprocate at different speeds between the forward path and the return path, periods determined at different times may be separately used for the forward path and the return path.

Third Embodiment of the Present Invention

In a third embodiment of the present invention, for the purpose of further improving the accuracy of the correction of the scanning, two photodetectors are arranged. According to this embodiment, even when the optical axis of the resonant scanner is shifted due to environmental change or the like, the scanning can be corrected taking the shift into consideration.

(Structure of Apparatus)

FIG. 9A and FIG. 9B are illustrations of arrangement of the photodetectors according to this embodiment. The structure of the apparatus according to this embodiment is similar to that in the second embodiment except that two photodetectors are arranged.

FIG. 9A is an illustration of the photodetectors observed from an angle that is the same as those in FIG. 4A and FIG. 7A. The photodetector 131 is the same as the photodetector in the second embodiment, and is arranged at the same location as that in the second embodiment. A photodetector 132 is a photodetector having the same structure as the photodetector 131. In FIG. 9A, the photodetector 132 is arranged at a position overlapping the photodetector 131. As can be seen from FIG. 9B in which the photodetectors are observed from a different angle, the photodetector 132 is arranged at a position substantially symmetrical to the photodetector 131 with respect to the Y axis, that is, at a position at which the angle of the photodetector 132 is substantially the opposite to that of the photodetector 131.

(Description of Correction of Scanning)

Correction of the scanning according to this embodiment is described with reference to FIG. 10. In this embodiment, instead of Expression (1) in the first embodiment and the second embodiment, the following expression is used.

$$x = A\cos(\omega t + \alpha) + B \qquad (7)$$

In Expression (7), a constant term B is added to Expression (1). The constant term B is the amount of shift of the optical axis of the resonant scanner from the optical axis of the apparatus. When the resonant scanner reciprocates once, detected times by the photodetector 131 arranged at the position x1 are represented by t1 and t2. Detected times by the photodetector 132 arranged at the position x1' are represented by t1' and t2'. The values of x1 and x1' are constants determined when the apparatus is adjusted.

Through solving four equations in which (t1, x1), (t2, x1), (t1', x1'), and (t2', x1'), respectively, are substituted in Expression (7), A, B, and α in Expression (7) can be determined as below:

$$\alpha = \pi - \phi \qquad (8)$$

$$A = \frac{x_1 - x_1'}{\cos\varphi' - \cos\varphi} \qquad (9)$$

$$B = \frac{x_1 \cos\varphi' - x_1' \cos\varphi}{\cos\varphi' - \cos\varphi} \qquad (10)$$

where $$\phi = \frac{\omega(t_2 + t_1)}{2} \quad \varphi = \frac{\omega(t_2 - t_1)}{2} \quad \varphi' = \frac{\omega(t_2' - t_1')}{2} \qquad (11)$$

is satisfied.

After that, similarly to the first and second embodiments, coordinates X1, X2, X3, . . . at which the signals are to be acquired are determined using Expression (4). Through substituting the coordinates in Expression (7), the times T1, T2, . . . , and Tn at which the signals are to be acquired can be acquired.

Here, attention is focused on Expression (10). When the difference between φ and φ' and the difference between x1 and x1' are small, both the denominator and the numerator on the right side of Expression (10) are small values, and thus, the accuracy of calculating B is lowered. Thus, it is desired that φ and φ' be different to some extent and x1 and x1' be different to some extent. This means that the two photodetectors are desirably placed away from each other. Therefore, according to this embodiment, the photodetector 131 and the photodetector 132 are arranged at positions substantially symmetrical to each other with respect to the Y axis. However, other arrangements are also possible insofar as A, α, and B in Expression (7) can be determined with sufficient accuracy.

Further, the positions of the photodetectors in FIG. 9A may be different from those in this embodiment. For example, the positions may overlap the optical axis illustrated in FIG. 9A. Even when the angles formed by the photodetectors and the optical axis are small in FIG. 9A, insofar as the photodetectors are away from the optical axis in FIG. 9B, the image can be picked up without impairing the scanning of the eye to be inspected.

Further, it is not necessary that the two photodetectors overlap each other in XZ plane as illustrated in FIG. 9A.

Figure 10:
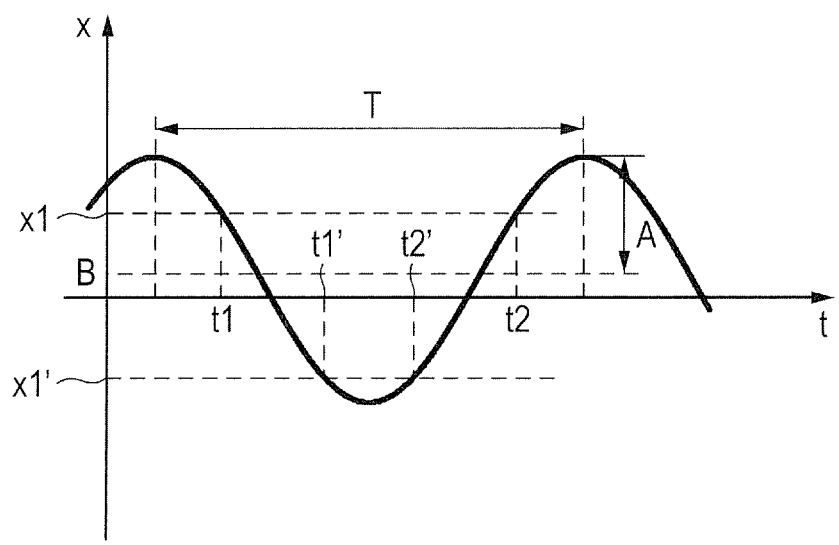
FIG. 10 is an explanatory view of a method of correcting scanning according to the third embodiment of the present invention.

When the angles of the two photodetectors are different from each other, through directing the galvano scanner to the respective angles in succession, all of the information shown in FIG. 10 can be acquired.

Further, three or more photodetectors may be arranged. Expression (1) and Expression (7) are on the precondition that the drive of the resonant scanner is represented by a trigonometric function, but a term that corrects the departure of the actual drive from the trigonometric function may be added. Further, a special function that suits the actual drive of the resonant scanner may be used.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

Further, while the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

For example, the position information generating unit according to the present invention is not limited to the scan-correcting chart or the photodetector. For example, a mirror may be used, or a line sensor or an area sensor may be used.

Further, the scanning unit configured to acquire the position using the position information generating unit is not limited to the resonant scanner, and a galvano scanner, a polygon scanner, or other scanning units may be used.

For example, in the above-mentioned embodiments, the case where an object to be inspected is an eye has been described, but the present invention can also be applied to objects to be measured other than an eye, such as skin and an organ. In this case, the present invention has an embodiment mode as medical image pickup equipment other than an ophthalmic image pickup apparatus, e.g., an endoscope. Thus, it is desired that the present invention be understood as an image pickup apparatus exemplified by an ophthalmic image pickup apparatus and the eye to be inspected be understood as an embodiment mode of an object to be inspected.

This application claims the benefit of Japanese Patent Application No. 2015-150573, filed Jul. 30, 2015, and Japanese Patent Application No. 2016-142945, filed Jul. 21, 2016, which are hereby incorporated by reference herein in their entirety.

What is claimed is:

1. An ophthalmic apparatus, comprising:
a scanning unit configured to scan a scanning area with measuring light emitted from a light source;
a detecting unit that is arranged at a position within the scanning area and outside of a measuring area of an eye to be inspected, wherein the measuring area is included within the scanning area and is an area acquiring image information of the eye to be inspected by scanning with the measuring light by the scanning unit;
a light receiving unit configured to receive return light of the measuring light from the eye to be inspected when the scanning unit is scanning the measuring area with the measuring light;
an acquiring unit configured to acquire information indicating a scan time of the scanning unit based on output from the detecting unit when the detecting unit detects the measuring light scanned by the scanning unit;
a correcting unit configured to correct sampling timing of sampling an output signal from the light receiving unit based on the information indicating the scan time; and
a sampling unit configured to sample the output signal as the image information based on the corrected sampling timing.

2. The ophthalmic apparatus according to claim 1, wherein the scanning unit is configured to scan a sensor surface of the detecting unit a plurality of times through reciprocating scanning with the measuring light, and
wherein the acquiring unit is configured to acquire the information indicating the scan time based on a plurality of outputs of the detecting unit corresponding to the plurality of times of the scanning.

3. The ophthalmic apparatus according to claim 2, wherein the scanning unit is configured to scan the measuring area of the eye to be inspected with the measuring light and to scan the sensor surface of the detecting unit with the measuring light in succession.

4. The ophthalmic apparatus according to claim 3, wherein the scanning unit is configured to scan the sensor surface of the detecting unit with the measuring light after scanning the measuring area of the eye to be inspected with the measuring light.

5. The ophthalmic apparatus according to claim 1, wherein the detecting unit is arranged at a position away from a center of the scanning area scanned by the scanning unit by a predetermined distance.

6. The ophthalmic apparatus according to claim 1, wherein the detecting unit comprises a plurality of detecting elements, and
wherein the acquiring unit is configured to acquire the information indicating the scan time based on output of the plurality of detecting elements.

7. The ophthalmic apparatus according to claim 1, further comprising an objective lens,
wherein the detecting unit is arranged between the objective lens and the scanning unit.

8. The ophthalmic apparatus according to claim 1, wherein the scanning unit comprises a resonant scanner, and wherein the detecting unit comprises a photodiode.

9. The ophthalmic apparatus according to claim 1, wherein the scanning unit is configured to perform scanning with the measuring light through reciprocation.

10. An ophthalmic apparatus, comprising:
a scanning unit configured to scan a scanning area with measuring light emitted from a light source;
a member that has a pattern thereon, and that is arranged at a position within the scanning area scanned by the scanning unit with the measuring light and outside of a measuring area of an eye to be inspected, wherein the measuring area is included within the scanning area and is an area acquiring image information of the eye to be inspected by scanning with the measuring light by the scanning unit;
a light receiving unit configured to receive (a) return light of the measuring light from the eye to be inspected and (b) return light of the measuring light from the member;
an acquiring unit configured to acquire information indicating a scan time of the scanning unit based on return light from the member irradiated with the measuring light when the scanning unit is scanning the member with the measuring light;
a correcting unit configured to correct sampling timing of sampling an output signal from the light receiving unit based on the information indicating the scan time; and
a sampling unit configured to sample the output signal from the light receiving unit as the image information based on the corrected sampling timing.

11. A correcting method comprising:
an acquiring step of acquiring information indicating a scan time of a scanning unit based on output from a detecting unit that is arranged at a position within a scanning area scanned by the scanning unit with measuring light and outside of a measuring area of an eye to be inspected, wherein the measuring area is included within the scanning area and is an area acquiring image information of the eye to be inspected by scanning with the measuring light by the scanning unit;
a correcting step of correcting sampling timing of an output signal based on the information indicating the scan time;
a light receiving step of receiving, when the scanning unit is scanning the measuring area of the eye to be inspected with the measuring light, return light of the measuring light from the eye to be inspected by using a light receiving unit, and outputting the output signal; and
a sampling step of sampling the output signal as the image information based on the corrected sampling timing,
wherein the acquiring step, the correcting step, the light receiving step, and the sampling step are repeatedly performed.

12. A non-transitory tangible medium configured to store a program for causing a computer to execute the correcting method of claim 11.

13. The ophthalmic apparatus according to claim 10, wherein the pattern includes a plurality of parallel lines which are drawn in parallel on the member.

\* \* \* \* \*